United States Patent [19]

Maetzke

[11] Patent Number: 5,616,590
[45] Date of Patent: Apr. 1, 1997

[54] PLANT MICROBICIDES

[75] Inventor: Thomas Maetzke, Münchenstein, Switzerland

[73] Assignee: Ciba-Geigy Corporation, Tarrytown, N.Y.

[21] Appl. No.: 474,054

[22] Filed: Jun. 7, 1995

[30] Foreign Application Priority Data

Jun. 30, 1994 [CH] Switzerland .............. 2093/94

[51] Int. Cl.$^6$ .............. A61K 31/435; C07D 513/04
[52] U.S. Cl. .............. 514/301; 504/246; 546/114
[58] Field of Search .............. 546/114; 514/301

[56] References Cited

U.S. PATENT DOCUMENTS

| | | | |
|---|---|---|---|
| 4,880,916 | 11/1989 | Adam | 534/606 |
| 4,931,581 | 6/1990 | Schurter et al. | 560/18 |
| 4,997,667 | 3/1991 | Nofre et al. | 426/548 |
| 5,260,423 | 11/1993 | Kunz et al. | 534/618 |

FOREIGN PATENT DOCUMENTS

A321368  6/1989  European Pat. Off. .

OTHER PUBLICATIONS

Abbas Shafiee, Journal of Heterocyclic Chemistry, Bd. 13, No. 2, (1976) pp. 301–304.

Temple, Jr., et al. J. Org. Chem., vol. 37, No. 23, 1972 pp. 3601–3604.

Temple, Jr., et al., J. Org. Chem, vol. 41, No. 24, 1976 pp. 3784–3788.

Cline et al., J. Org. Chem., vol. 43, No. 26, 1978 pp. 4910–4915.

*Primary Examiner*—Bernard Dentz
*Attorney, Agent, or Firm*—Edward McC. Roberts

[57] ABSTRACT

Compounds of the formula I

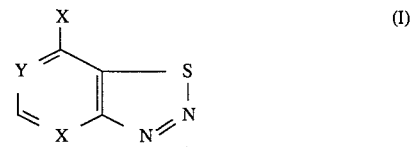

in which a) X is CH and Y is N; or b) X is N and Y is CH; and in which Z is a $C_1$ group to which there are bonded 1–3 halogen atoms or 1–3 substituted or unsubstituted hetero atoms O, S and/or N are suitable for controlling and preventing microbial attack on plants.

23 Claims, No Drawings

PLANT MICROBICIDES

The invention relates to novel microbicidally active compounds of the formula I

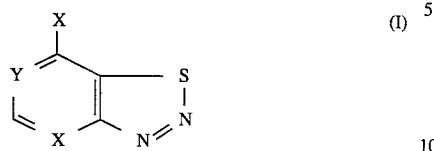

in which
a) X is CH and Y is N; or
b) X is N and Y is CH; and in which
Z is a $C_1$ group to which there are bonded 1–3 halogen atoms or 1–3 substituted or unsubstituted hetero atoms O, S and/or N; in free form or in salt form.

The invention furthermore relates to the preparation of these compounds, to agrochemical compositions comprising, as active ingredient, at least one of these compounds, and to the use of the active ingredients or the compositions for protecting plants against attack by harmful microorganisms, in particular phytopathogenic fungi.

The compounds of the formula I and, if appropriate, the tautomers thereof can exist as salts. Compounds of the formula I which have at least one basic centre can form acid addition salts. These are formed, for example, with mineral acids, for example sulfuric acid, a phosphorus acid or a hydrohalic acid, with organic carboxylic acids, for example acetic acid, oxalic acid, malonic acid, maleic acid, fumaric acid or phthalic acid, with hydroxycarboxylic acids, for example ascorbic acid, lactic acid, malic acid, tartaric acid or citric acid, or with benzoic acid, or with organic sulfonic acids, for example methane- or p-toluenesulfonic acid.

Furthermore, compounds of the formula I which have at least one acidic group can form salts with bases. Examples of suitable salts with bases are metal salts, such as alkali metal salts or alkaline earth metal salts, for example sodium salts, potassium salts or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. If appropriate, corresponding internal salts can furthermore be formed. Preferred within the scope of the invention are agrochemically advantageous salts.

Unless otherwise defined, the general terms used hereinabove and hereinbelow have the meanings given below:

Hydrocarbon radicals can be saturated or unsaturated, open-chain or cyclic, or a mixture of open-chain and cyclic, for example cyclopropylmethyl or benzyl.

Alkyl groups are straight-chain or branched, depending on the number of carbon atoms, and are, for example, methyl, ethyl, n-propyl, isopropyl, n-butyl, sec-butyl, isobutyl, tert-butyl, sec-amyl, tert-amyl, 1-hexyl or 3-hexyl.

Unsaturated hydrocarbon radicals are alkenyl, alkynyl or alkenynyl groups with not more than 3 multiple bonds, for example butadienyl, hexatrienyl, 2-penten-4-ynyl.

Alkenyl is to be understood as straight-chain or branched alkenyl, for example allyl, methallyl, 1-methylvinyl or but-2-en-1-yl. Alkenyl radicals with a chain length of 3 to 4 carbon atoms are preferred.

Equally, alkynyl can be straight-chain or branched, depending on the number of carbon atoms, for example propargyl, but-1-yn-1-yl or but-1-yn-3-yl. Propargyl is preferred.

Cyclic unsaturated hydrocarbon radicals can be aromatic, for example phenyl and naphthyl, or nonaromatic, for example cyclopentenyl, cyclohexenyl, cycloheptenyl and cyclooctadienyl, or partially aromatic, for example tetrahydmnaphthyl and indanyl.

Halogen or halo is fluorine, chlorine, bromine or iodine, preferably fluorine, chlorine or bromine.

Haloalkyl can have identical or different halogen atoms, for example fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl or 3,3,3-trifluoropropyl.

Alkoxy is, for example, methoxy, ethoxy, propyloxy, i-propyloxy, n-butyloxy, iso-butyloxy, sec-butyloxy and tert-butyloxy; preferably methoxy and ethoxy.

Haloalkoxy is, for example, difluoromethoxy, trifluoromethoxy, 2,2,2-trifluoroethoxy, 1,1,2,2-tetrafluoroethoxy, 2-fluoroethoxy, 2-chloroethoxy and 2,2-difluoroethoxy.

Cycloalkyl is cyclopropyl, cyclobutyl, cyclopentyl or cyclohexyl, depending on the size of the ring.

Alkanoyl is either straight-chain or branched, in each case taking into consideration the number of carbon atoms included in each individual case, examples being formyl, acetyl, propionyl, butyryl, pivaloyl or octanoyl.

A heterocyclyl radical is to be understood as meaning 5- or 6-membered, aromatic and non-aromatic tings having the hetero atoms N, O and/or S. Furthermore, an unsubstituted or substituted benzo group may be fused to such a heterocyclyl radical which is bonded to the remaining moiety. Examples of heterocyclyl groups are pyridyl, pyrimidinyl, imidazolyl, thiazolyl, 1,3,4-thiadiazolyl, triazolyl, thienyl, furanyl, pyrrolyl, morpholinyl, oxazolyl and the corresponding partially or fully hydrogenated rings. Examples of heterocyclyl groups with fused benzo group are quinolyl, isoquinolyl, benzoxazolyl, quinoxalinyl, benzothiazolyl, benzimidazolyl, indolyl or indolinyl.

All the above enumerations are by way of example and do not represent any limitation.

Preferred groups are:
(1) Compounds of the formula I in which:
Z is CN, CO—A, CS—A, CH=U, $CH_2$—V, CH(—V)$_2$ or C(—V)$_3$; and in which furthermore the remaining substituents are as follows:

A is $OR_2$, $SR_2$, $N(R_3)R_4$, $N(R_5)$—$OR_6$, O—$N(=C)_n(R_7)R_8$ or $N(R_9)$—$N(=C)_n(R_7)R_8$;

U is O, $NR_{10}$, N—$OR_6$ or N—$N(=C)_n(R_7)R_8$;

V is halogen, hydroxyl, $C_1$–$C_4$alkoxy, $C_1$–$C_4$acyloxy, benzoyloxy, benzyloxy, or two V together with the carbon atom to which they are bonded are a cyclic acetal group;

n is 0 or 1;

$R_2$ to $R_{10}$ are hydrogen, a substituted or unsubstituted open-chain, saturated or unsaturated hydrocarbon radical having up to 8 carbon atoms, a substituted or unsubstituted cyclic, saturated or unsaturated hydrocarbon radical having up to 10 carbon atoms, substituted or unsubstituted benzyl or phenethyl, a substituted or unsubstituted acyl group having up to 8 carbon atoms, a substituted or unsubstituted benzoyl group, or a substituted or unsubstituted heterocyclyl radical; or $R_3$ and $R_4$ together with the nitrogen atom to which they are bonded are a 5- or 6-membered, substituted or unsubstituted heterocycle; or $R_7$ and $R_8$ together with the atom to which they are bonded are a 5- or 6-membered carbocyclic or heterocyclic ring, the abovementioned rings being unsubstituted or substituted; in free form or in salt form.

(2) Compounds of the formula I in which:
$R_2$ and $R_3$ are hydrogen, $C_1$–$C_8$alkyl which is unsubstituted or substituted by 1–5 halogen atoms, $C_3$–$C_6$cycloalkyl, $C_1-C_4$alkoxy, phenoxy, hydroxyl, nitro, cyano, $C_1-C_4$alkanoyl, benzoyl, carboxyl, $C_1-C_4$alkoxycarbonyl, benzyloxycarbonyl, $C_1-C_4$acyloxy, benzoyloxy, $C_1-C_4$dialkylamino or heterocyclyl, $C_3-C_6$alkenyl which is unsubstituted or substituted by 1–5 halogen atoms, or are $C_3-C_6$alkynyl, $C_3-C_6$cycloalkyl, phenyl, benzyl or phenethyl, the phenyl rings of these compounds being unsubstituted or mono- to trisubstituted by halogen, hydroxyl, $C_1-C_4$alkyl, halo-$C_1-C_2$alkyl, $C_1-C_2$alkoxy, halo-$C_1-C_2$-alkoxy or nitro, naphthyl, $C_1-C_4$alkanoyl, benzoyl, or are heterocyclyl which is unsubstituted or mono- to trisubstituted by identical or different substituents from the series consisting of halogen, $C_1-C_2$alkyl, halomethyl or nitro;

$R_4$ is hydrogen, $C_1-C_6$alkyl, $C_3-C_6$alkenyl, $C_3-C_6$alkynyl, $C_3-C_6$cycloalkyl, phenyl or benzyl, the phenyl rings of these compounds being unsubstituted or mono- to disubstituted by halogen, hydroxyl, $C_1-C_2$alkyl, $C_1-C_2$alkoxy, halomethyl or nitro; or $R_3$ and $R_4$ together with the nitrogen atom to which they are bonded are a 5- or 6-membered heterocycle which is unsubstituted or mono- to trisubstituted by $C_1-C_2$alkyl; $R_5$, $R_6$, $R_7$, $R_8$, $R_9$ and $R_{10}$ independently of one another are hydrogen, $C_1-C_6$alkyl, $C_3-C_6$alkenyl, $C_3-C_6$alkynyl, $C_3-C_6$cycloalkyl, phenyl or benzyl, the phenyl rings of these compounds being unsubstituted or mono- to disubstituted by halogen, hydroxyl, $C_1-C_2$alkyl, $C_1-C_2$alkoxy, halo-$C_1-C_2$alkyl or nitro; or $R_7$ and $R_8$ together with the atom to which they are bonded are a 5- to 7-membered carbocyclic or heterocyclic ring, the abovementioned rings being unsubstituted or mono- to trisubstituted by identical or different substituents from the series consisting of halogen, $C_1-C_2$alkyl, halo-$C_1-C_2$alkyl or nitro.

(3) Compounds of the formula I in which:

$R_2$ and $R_3$ are hydrogen, $C_1-C_5$alkyl which is unsubstituted or substituted by 1–3 halogen atoms, $C_3-C_6$cycloalkyl, $C_1-C_2$alkoxy, phenoxy, hydroxyl, nitro, cyano, $C_1-C_2$alkanoyl, benzoyl, carboxyl, $C_1-C_4$alkoxycarbonyl, benzyloxycarbonyl, $C_1-C_2$acyloxy, benzoyloxy, $C_1-C_4$dialkylamino or heterocyclyl or $C_3-C_4$alkenyl which is unsubstituted or substituted by 1–3 halogen atoms, $C_3-C_4$alkynyl, $C_3-C_6$cycloalkyl, phenyl, benzyl or phenethyl, the phenyl rings of these compounds being unsubstituted or mono- to disubstituted by halogen, hydroxyl, $C_1-C_4$alkyl, halo-$C_1-C_2$alkyl, $C_1-C_2$alkoxy, halo-$C_1-C_2$alkoxy, or by nitro, or are naphthyl or heterocyclyl, unsubstituted or mono- to disubstituted by identical or different substituents from the series consisting of halogen, $C_1-C_2$alkyl, halomethyl or nitro;

$R_4$ is hydrogen, $C_1-C_4$alkyl, $C_3-C_4$alkenyl, $C_3-C_4$alkynyl, $C_3-C_6$cycloalkyl, phenyl or benzyl;

$R_3$ and $R_4$ together with the nitrogen atom to which they are bonded are pyrrolidine, piperidine, morpholine or dimethylmorpholine;

$R_5$, $R_6$, $R_7$, $R_8$, $R_9$ and $R_{10}$ independently of one another are hydrogen, $C_1-C_4$alkyl, $C_3-C_4$alkenyl, $C_3-C_4$alkynyl, $C_3-C_6$cycloalkyl, phenyl or benzyl, the phenyl rings of these compounds being unsubstituted or mono- to disubstituted by halogen, hydroxyl, $C_1-C_2$alkyl, $C_1-C_2$alkoxy, halomethyl or nitro; or $R_7$ and $R_8$ together with the atom to which they are bonded are a 5- to 7-membered carbocyclic or heterocyclic ring, the abovementioned rings being unsubstituted or mono- to disubstituted by identical or different substituents from the series consisting of halogen, methyl, halomethyl or nitro.

(4) Compounds of the formula I in which:

Z is CO—A;

A is $OR_2$, $SR_2$, $N(R_3)R_4$, $N(R_5)$—$OR_6$, O—N(=C)$_n$($R_7$)$R_8$ or $N(R_9)$—N(=C)$_n$($R_7$)$R_8$; of these in particular those in which A is $OR_2$ or $SR_2$;

$R_2$ to $R_9$ being as defined in formula I.

(5) Preferred amongst the compounds mentioned under (4) are those in which $R_2$ is hydrogen, $C_1-C_5$alkyl which is unsubstituted or substituted by 1–3 halogen atoms, $C_3-C_6$cycloalkyl, $C_1-C_2$alkoxy, phenoxy, hydroxyl, nitro, cyano, $C_1-C_2$alkanoyl, benzoyl, carboxyl, $C_1-C_4$alkoxycarbonyl, benzyloxycarbonyl, $C_1-C_2$acyloxy, benzoyloxy, $C_1-C_4$dialkylamino or heterocyclyl, or $C_3-C_4$alkenyl which is unsubstituted or substituted by 1–3 halogen atoms, $C_3-C_4$alkynyl, $C_3-C_6$cycloalkyl, phenyl, benzyl or phenethyl, the phenyl rings of these compounds being unsubstituted or mono- to disubstituted by halogen, hydroxyl, $C_1-C_4$alkyl, halo-$C_1-C_2$alkyl, $C_1-C_2$alkoxy, halo-$C_1-C_2$alkoxy or nitro, or naphthyl or heterocyclyl, unsubstituted or mono- to disubstituted by identical or different substituents from the series consisting of halogen, $C_1-C_2$alkyl, halomethyl or nitro;

and particularly preferred are those in which $R_2$ is hydrogen, $C_1-C_5$alkyl, propenyl, phenyl or benzyl, the phenyl rings of these compounds being unsubstituted or mono- to disubstituted by halogen.

(6) Compounds of the formula I in which

Z is CO—$OR_2$ and in which $R_2$ is as defined in formula I.

(7) Compounds of the formula I in which:

Z is CN or CO—N($R_3$)$R_4$;

$R_3$ is hydrogen, $C_1-C_5$alkyl which is unsubstituted or substituted by 1–3 halogen atoms, $C_3-C_6$cycloalkyl, $C_1-C_2$alkoxy, phenoxy, hydroxyl, nitro, cyano, $C_1-C_2$alkanoyl, benzoyl, carboxyl, $C_1-C_4$alkoxycarbonyl, benzyloxycarbonyl, $C_1-C_2$acyloxy, benzoyloxy, $C_1-C_4$dialkylamino or heterocyclyl, or $C_3-C_4$alkenyl which is unsubstituted or substituted by 1–3 halogen atoms, or $C_3-C_4$alkynyl, $C_3-C_6$cycloalkyl, phenyl, benzyl or phenethyl, the phenyl rings of these compounds being unsubstituted or mono- to disubstituted by halogen, hydroxyl, $C_1-C_4$alkyl, halo-$C_1-C_2$alkyl, $C_1-C_2$alkoxy, halo-$C_1-C_2$alkoxy or nitro, or naphthyl or heterocyclyl, unsubstituted or mono- to disubstituted by identical or different substituents from the series consisting of halogen, $C_1-C_2$alkyl, halomethyl or nitro;

$R_4$ is hydrogen, $C_1-C_4$alkyl, $C_3-C_4$alkenyl, $C_3-C_4$alkynyl, $C_3-C_6$cycloalkyl, phenyl or benzyl;

$R_3$ and $R_4$ together with the nitrogen atom to which they are bonded are pyrrolidine, piperidine, morpholine or dimethylmorpholine.

(8) Compounds of the formula I in which:

Z is CO—N($R_3$)$R_4$;

$R_3$ is hydrogen, $C_1-C_5$alkyl which is unsubstituted or substituted by $C_1-C_4$alkoxycarbonyl or benzyloxycarbonyl, or $C_3-C_4$alkenyl, $C_3-C_4$alkynyl, $C_3-C_6$cycloalkyl, phenyl or benzyl, the phenyl rings of these compounds being unsubstituted or mono- to disubstituted by halogen, hydroxyl, methyl, methoxy, halomethyl, halomethoxy or nitro;

$R_4$ is hydrogen or methyl; or $R_3$ and $R_4$ together with the nitrogen atom to which they are bonded are pyrrolidine, piperidine, morpholine or dimethylmorpholine.

(9) Compounds of the formula I in which:

Z is CS—A;

A is $OR_2$, $SR_2$ or $N(R_3)R_4$;

$R_2$ and $R_3$ are hydrogen, $C_1-C_5$alkyl which is unsubstituted or substituted by 1–3 halogen atoms, $C_3-C_6$cycloalkyl, $C_1$–$C_2$alkoxy, phenoxy, hydroxyl, nitro, cyano, $C_1$–$C_2$alkanoyl, benzoyl, carboxyl, $C_1$–$C_4$alkoxycarbonyl, benzyloxycarbonyl, $C_1$–$C_2$acyloxy, benzoyloxy, $C_1$–$C_4$dialkylamino or heterocyclyl, or $C_3$–$C_4$alkenyl which is unsubstituted or substituted by 1–3 halogen atoms, or $C_3$–$C_4$alkynyl, $C_3$–$C_6$cycloalkyl, phenyl, benzyl or phenethyl, the phenyl rings of these compounds being unsubstituted or mono- to disubstituted by halogen, hydroxyl, $C_1$–$C_4$alkyl, halo-$C_1$–$C_2$alkyl, $C_1$–$C_2$alkoxy, halo-$C_1$–$C_2$alkoxy or nitro, or naphthyl or heterocyclyl, unsubstituted or mono- to disubstituted by identical or different substituents from the series consisting of halogen, $C_1$–$C_2$alkyl, halomethyl or nitro;

$R_4$ is hydrogen, $C_1$–$C_4$alkyl, $C_3$–$C_4$alkenyl, $C_3$–$C_4$alkynyl, $C_3$–$C_6$cycloalkyl, phenyl or benzyl;

$R_3$ and $R_4$ together with the nitrogen atom to which they are bonded are pyrrolidine, piperidine, morpholine or dimethylmorpholine.

(10) Compounds of the formula I in which:

Z is CN, CH=U or $CH_2$—V;

U is O, $NR_{10}$, N—$OR_6$ or N—$N(=C)_n(R_7)R_8$;

V is halogen, hydroxyl, $C_1$–$C_4$alkoxy, $C_1$–$C_4$acyloxy, benzoyloxy or benzyloxy; and in which $R_6$, $R_7$, $R_8$ and $R_{10}$ are as defined in formula I; and n is 0 or 1.

(11) Compounds of the formula I in which:

Z is $CH(V)_2$; and

V is $C_1$–$C_4$alkoxy or a 5- or 6-membered cyclic acetal.

(12) Compounds of the formula I in which:

Z is CN, COOH, CHO, $CH_2OH$, $CH_2Cl$, $CCl_3$ $CHF_2$ or $CF_3$.

(13) Compounds of the formula Ia (Ia)

in which Z is as defined in formula I.

(14) Compounds of the formula Ib (Ib)

in which Z is as defined in formula I.

Compounds of the formula Ia in which Z is CO—$N(alkyl)_2$ or COOH can be prepared in accordance with synthesis scheme 1 as follows:

(1) Reaction of a compound of the formula VI with diethylthiocarbamoyl chloride, (prepared by the method of M. Vilkas, D. Qasmi, Synth. Commun. 20, 2769, (1990)), in an inert polar solvent such as DMF or DMPU at 0°–10° C. in the presence of a base, such as triethylamine, to give a compound of the formula VII;

(2) Metalation of a compound of the formula VII with an organometallic compound, such as lithium 2,2,4,4-tetramethylpiperidide (LTMP) or lithium diisopropylamide, in an aprotic solvent, such as THF or hexane, at –100° C. to +10° C., reaction of the metal complex formed with tosyl azide (prepared by the method of W. v. Doering, C. H. DePuy, J. Chem. Soc. 5956, (1953) or diphenyl azidophosphate to give a compound of the formula VIII; (¾) Reduction of the azido group with a complex hydride, for example with $NaBH_4$, in methanol at 0°–30° C., resulting directly in the rearranged compound of the formula IIa1.

(5) Diazotization of a compound of the formula IIa1 with an inorganic or organic nitrite, for example with isoamyl nitrite in an inert solvent, such as dimethoxyethane, to give a compound of the formula Ia1.

(6) If desired, hydrolysis of the amido group in compound Ia1 to the carboxyl group of the compound Ia2.

Synthesis scheme 1

Furthermore, compounds of the formula Ia in which Z is COOalkyl or COOH can be prepared in accordance with synthesis scheme 2 analogously to known processes by the method of B. Blank et al., J. Med. Chem. 17, 1065, (1974); B. Blank et al., ibid. 20, 1572, (1977), as follows:

(7) Oxidation of a compound of the formula XI with peracids, for example m-chloroperbenzoic acid, in chloroform to give the N-oxide of the formula XII;

(8) nitration of the N-oxide, and subsequently (9) reaction with a thiol of the formula HS-W or a salt thereof, W being a substituted or unsubstituted $C_1$-$C_{12}$hydrocarbon, to give a compound of the formula XIV;

(10) Reduction of the nitro and the N-oxide group, for example with iron powder in aqueous acid or with hydrogen/catalyst to give a compound of the formula IIa2;

(11) Diazotization of a compound of the formula IIa2 with an inorganic or organic nitrite, for example isoamyl nitrite, in an inert solvent, such as dimethoxyethane, to give a compound of the formula Ia3;

and, if desired, hydrolysis of the ester group in compound Ia3 to the carboxyl group of the compound Ia2.

Particular emphasis must be placed on the reaction step in which compounds of the formula Ia are prepared by diazotizing a compound of the formula IIa

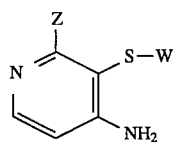

in which Z is as defined for formula I and

W is a substituted or unsubstituted $C_1$-$C_{12}$hydrocarbon or a substituted or unsubstituted carbamoyl group, with an inorganic or organic nitrite, for example isoamyl nitrite, in an inert solvent, for example dimethoxyethane.

Compounds of the formula Ib in which Z is CO—N(alkyl)$_2$ or COOH can be prepared in accordance with synthesis scheme 3 as follows:

(12/13) Metalation of a compound of the formula XV with lithium 2,2,6,6-tetramethyl-piperidine Synthesis scheme 2

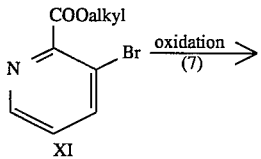

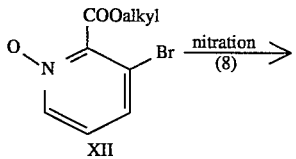

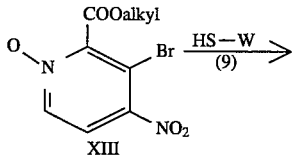

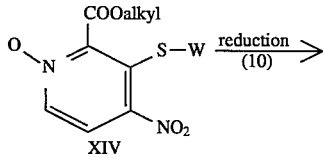

-continued
Synthesis scheme 2

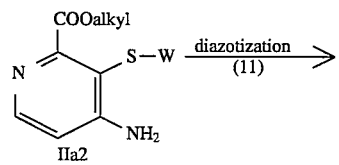

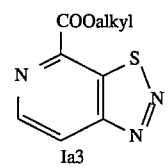

Synthesis scheme 3

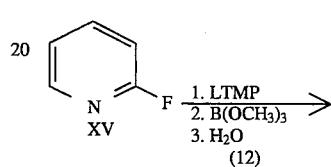

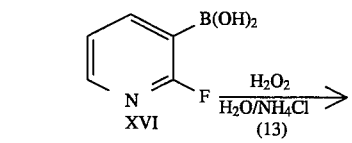

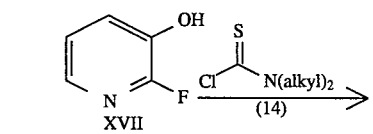

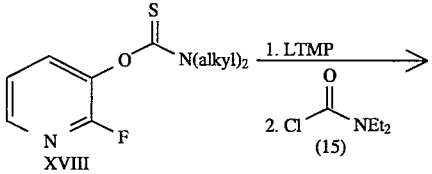

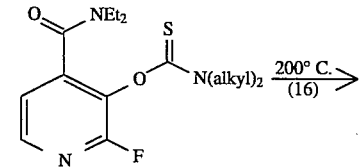

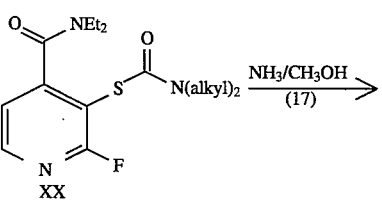

-continued
Synthesis scheme 3

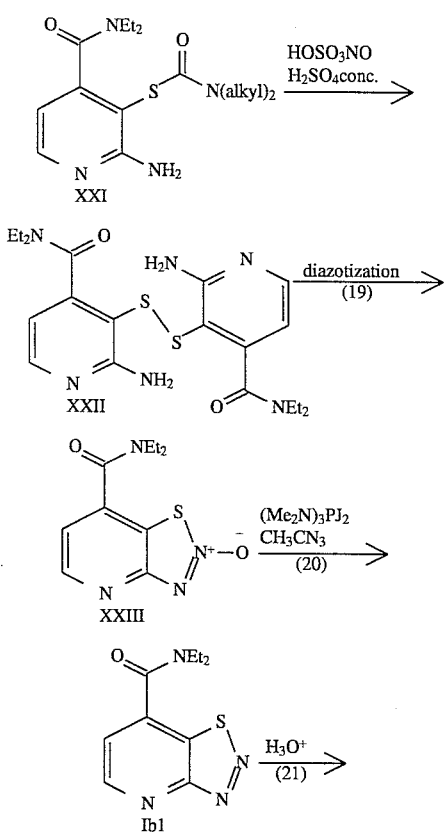

(LTMP). Reaction with trimethyl borate followed by oxidation, for example with $H_2O_2$, to give a compound of the formula XVII.

(14) Reaction with diethylthiocarbamoyl chloride to give a compound of the formula XVIII.

(15) Metalation with LTMP followed by reaction with diethylcarbamoyl chloride to give a compound of the formula XIX.

(16) Rearrangement at 200° C., for example in diphenyl ether, to give a compound of the formula XX:

(17) Aminolysis with $NH_3$ to give a compound of the formula XXI.

(18) Reaction with nitrosylsulfuric acid in concentrated sulfuric acid to give the corresponding disulfide of the formula XXII.

(19) Diazotization with an inorganic or organic nitrite, for example isoamyl nitrite, in an inert solvent, for example dimethoxyethane, to give the N-oxide of the formula XXIII.

(20) Reduction (for example with iodine/tris(dimethylamino)phosphine to give a compound of the formula Ib1; and, if desired, hydrolysis of the amido group in the compound Ib1 to the carboxyl group of the compound Ib2.

Particular emphasis must be placed on the reaction step in which compounds of the formula Ib are prepared by reducing a compound of the formula XXIII,

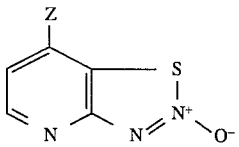

in which Z is as defined for formula I, with a reducing agent, for example with $I_2$/tris(dimethylamino)phosphine, hydrazine, iron(II) salts or sodium borohydride.

Compounds of the formula I in which Z is COOH can be converted by known methods to give other compounds of the general formula I in which Z is as defined above. For example, the carboxylic acids can be converted with thionyl chloride to give the corresponding carboxylic acid chlorides, in which the group Z can be converted in accordance with synthesis scheme 4, as follows:

Synthesis scheme 4: Conversion of the group Z

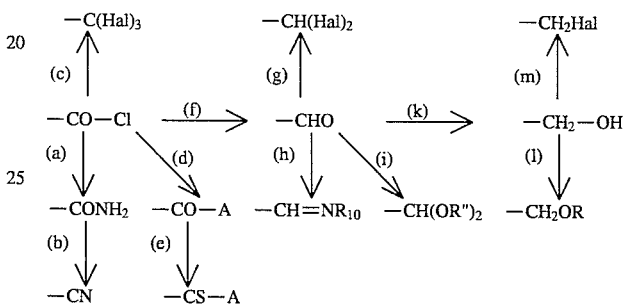

(a) $NH_3$;
(b) Dehydrating agent, for example $SOCl_2$ or $COCl_2$;
(c) Halogenating agent, for example $PCl_5$ or $SF_4$;
(d) M-A (III) in which M is hydrogen, $Li^+$, $Na^+$, $K^+$, ½ $Mg^{2+}$ or a quaternary ammonium ion and A is as defined for formula I;
(e) Thionating agent, for example phosphorus pentasulfide or 4-methoxyphenylthiophosphonic cyclodithio anhydride "Lawesson reagent");
(f) Reduction, for example with hydrogen/catalyst;
(g) Halogenating agent, for example $PCl_5$ or $SF_4$;
(h) $H_2NR_{10}$ in which $R_{10}$ is as defined for formula I;
(i) $C_1$–$C_4$alcohol or $C_2$–$C_3$diol;
(k) Reduction, for example with hydrogen/catalyst or with a complex hydride, for example $LiAlH_2(OCH_2CH_2OCH_3)_2$;
(l) L-R' in which L is a leaving group and R' is $C_1$–$C_4$alkyl, $C_1$–$C_4$acyl, benzoyl or benzyl;
(m) Halogenating agent, for example $POCl_3$, $SOCl_2$, $PBr_3$ or $SF_4$.

The reactions described are carried out in a manner known per se, for example in the absence or, conventionally, in the presence of a suitable solvent or diluent or a mixture of these, the process being carried out, as required, with cooling, at room temperature or with heating, for example in a temperature range from approximately −80° C. to the boiling point of the reaction medium, preferably from approximately −20° C. to approximately +150° C., and, if required, in a sealed vessel, under pressure, under an inert gas atmosphere and/or under anhydrous conditions. Reactions with organometallic compounds, for example lithium 2,2,6,6-tetramethylpiperidide, are advantageously carried out at −100° C. to +10° C. Diazotizations, i.e. the reaction of a primary amine with nitrous acid or with an inorganic or organic nitrite are advantageously carried out at −20° C. to +30° C.

Examples of leaving groups are fluorine, chlorine, bromine, iodine, $C_1$–$C_8$alkylthio, such as methylthio, ethylthio or propylthio, $C_1$–$C_8$alkanoyloxy, such as acetoxy, (halo-) $C_1$–$C_8$alkanesulfonyloxy, such as methanesulfonyloxy, ethanesulfonyloxy or trifluoromethanesulfonyloxy, or substituted or unsubstituted phenylsulfonyloxy, such as benzenesulfonyloxy or p-toluenesulfonyloxy, imidazolyl, hydroxyl or water.

Examples of suitable bases are the hydroxides, hydrides, amides, alkanolates, carbonates, dialkylamides or alkylsilylamides of alkali metals or alkaline earth metals, alkylamines, alkylenediamines, free or N-alkylated, saturated or unsaturated cycloalkylamines, basic heterocycles, ammonium hydroxides and carbocyclic amines. Examples which may be mentioned are sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyltrimethylammonium hydroxide and 1,8-diazabicyclo[5.4.0]undec-5-ene (DBU).

The reactants can be reacted with each other as such, i.e. without an addition of a solvent or diluent, for example in the melt. In most cases, however, it is advantageous to add an inert solvent or diluent or a mixture of these. The following may be mentioned as examples of such solvents or diluents: aromatic, aliphatic and alicyclic hydrocarbons and halohydrocarbons, such as benzene, toluene, xylene, chlorobenzene, bromobenzene, petroleum ether, hexane, cyclohexane, dichloromethane, trichloromethane, dichloroethane or trichloroethane; ethers, such as diethyl ether, tert-butyl methyl ether, tetrahydrofuran or dioxane; ketones, such as acetone or methyl ethyl ketone; alcohols, such as methanol, ethanol, propanol, butanol, ethylene glycol or glycerol; esters, such as ethyl acetate or butyl acetate; amides, such as N,N-dimethylformamide, N,N-dimethylacetamide, N-methylpyrrolidone or hexamethylphosphoric triamide; nitriles, such as acetonitrile; and sulfoxides, such as dimethyl sulfoxide. Bases employed in an excess, such as triethylamine, pyridine, N-methylmorpholine or N,N-diethylaniline, may also act as solvents or diluents.

The reaction can also be carded out with phase transfer catalysis in an organic solvent, for example methylene chloride or toluene, in the presence of an aqueous basic solution, for example sodium hydroxide solution, and of a phase transfer catalyst, for example tetrabutylammonium hydrogen sulfate.

Typical reaction conditions can be found in the examples.

In the event that the compounds of the formula I can exist as various stereoisomers, the invention relates to the pure isomers as well as to all isomer mixtures which are possible.

Novel starting materials and intermediates for the preparation of the compounds of the formula I, as well as the use and processes for the preparation of these starting materials and intermediates are also provided by the invention.

Thiadiazolo[4,5-b]pyridines of the formula XXX

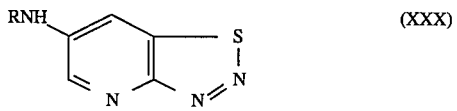

in the form of 6-amino derivatives have been disclosed in EP-A-321 368 and EP-A-321 369 for use as sweeteners. However, the abovementioned references do not give examples or preparation methods.

J. Org. Chem., Vol.43, 4910–5 (1978); and Vol. 41, 3784–8 (1976) describe diaminothiadiazolo[4,5-c]pyridines of the formula XXXI,

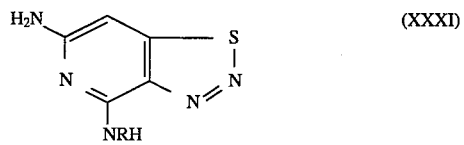

J. Org. Chem., Vol. 37, 3601–4 (1972) describes aminothiadiazolo[4,5-c]pyridines of the formula XXXII and aminothiadiazolo[5,4-b]pyridines of the formula XXXIII

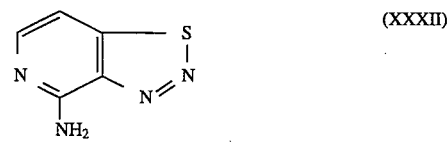

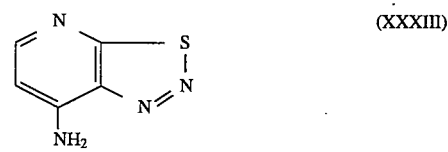

without proposing a use for the compounds XXXI, XXXII and XXXIII.

Compounds of the formula I differ characteristically from the abovementioned prior-art compounds with regard to their structure. Furthermore, they have an unexpectedly high microbicidal activity. Protection of the plants can be effected both by direct action on the pest and by activating and stimulating the plant's defence system (immunization). This immunizing action allows the treated plants to remain strong and healthy on their own accord without applying other microbicidal substances during the vegetation period.

The compounds of the formula I can be employed preventively and/or curatively as active ingredients in the control of plant pests in the agricultural sector and in related fields. The active ingredients of the formula I according to the invention are distinguished by an outstanding activity, even when applied at low use concentrations, and by being well tolerated by plants and environmentally friendly. They have highly advantageous, in particular systemic, properties and can be employed for protecting a large number of crop plants. The active ingredients of the formula I allow the pests which occur on plants or parts of plants (fruits, flowers, foliage, stalks, tubers, roots) in a variety of crops of useful plants to be contained or destroyed, and even parts of plants which are formed at a later point in time remain unharmed, for example by phytopathogenic microorganisms.

Furthermore, the compounds I can be employed as seed-dressing products for the treatment of seed (fruits, tubers, grains) and nursery plants as a protection against fungal infection and against soil-borne phytopathogenic fungi.

The compounds I are effective for example against phytopathogenic fungi belonging to the following classes: Fungi imperfecti (for example Botrytis, Pyricularia, Helminthosporium, Fusarium, Septoria, Cercospora und Altemaria) and Basidiomycetes (for example Rhizoctonia, Hemileia, Puccinia). Moreover, they are active against the classes of the Ascomycetes (for example Venturia and Erysiphe, Podosphaera, Monilinia, Uncinula) and of the Oomycetes (for example Phytophthora, Pythium, Plasmopara).

Target crops for the crop-protecting use within the scope of the invention are, for example, the following plant species: cereals (wheat, barley, rye, oats, rice, maize, Sorghum and related species); beet (sugar and fodder beet);

palmaceous fruit, stone fruit and soft fruit (apples, pears, plums, peaches, almonds, cherries, strawberries, raspberries and blackberries); leguminous plants (beans, lentils, peas, soya beans); oil crops (rape, mustard, poppies, olives, sunflowers, coconut, castor, cocoa, groundnuts); cucurbits (pumpkin, cucumbers, melons); fibre plants (cotton, flax, hemp, jute); citrus fruit (oranges, lemons, grapefruits, tangerines); vegetables (spinach, lettuce, asparagus, cabbages, carrots, onions, tomatoes, potatoes, bell peppers); the laurel family (avocado, Cinnamonium, camphor), and plants such as tobacco, nuts, coffee, aubergines, sugarcane, tea, pepper, vines, hops, the plantain family, natural rubber plants, and ornamentals.

Active ingredients I are conventionally used in the form of compositions and can be applied to the area or plant to be treated either in succession or simultaneously with other active ingredients. These other active ingredients can be, for example, fertilizers, trace element mediators or other products which affect plant growth. It is also possible to use selective herbicides as well as insecticides, fungicides, bactericides, nematicides, molluscicides or mixtures of a plurality of these compositions, if appropriate together with other carriers, surfactants or application-enhancing additives conventionally used in the art of formulation.

Suitable carriers and additives can be liquid or solid and are substances advantageously used in the art of formulation, for example natural or regenerated mineral substances, solvents, dispersants, wetting agents, tackifiers, thickeners, binders or fertilizers.

A preferred method of applying an active ingredient of the formula I or an agrochemical composition comprising at least one of these active ingredients is application to the foliage (foliar application). Frequency and rate of application depend on the risk of infestation with the pathogen in question. Alternatively, the active ingredients I can reach the plant via the soil through the root system (systemic action), by drenching the site of the plant with a liquid composition or by incorporating the substances into the soil in solid form, for example in the form of granules (soil application). In the case of paddy rice, such granules can be metered into the flooded paddy field. Alternatively, the compounds I can be applied to seeds for seed treatment (coating), either by soaking the grains or tubers in a liquid composition of the active ingredient or by coating them with a solid composition.

The compounds I are employed in pure form or, preferably, together with the auxiliaries conventionally used in the art of formulation. To this end, they are processed in a known manner, advantageously to give, for example, emulsion concentrates, spreadable pastes, directly sprayable or dilutable solutions, dilute emulsions, wettable powders, soluble powders, dusts or granules, for example by encapsulation in polymeric substances. The methods of application, such as spraying, atomizing, dusting, scattering, brushing on or pouring, as well as the type of composition are selected to suit the intended aims and the prevailing circumstances.

Advantageous rates of application are generally 5 g to 2 kg of active ingredient (a.i.) per hectare (ha), preferably 10 g to 1 kg of a.i./ha, in particular 20 g to 600 g of a.i./ha. When used as seed-dressing agents, it is advantageous to use doses from 10 mg to 1 g of active ingredient per kg of seed.

The formulations, i.e. the compositions, products or preparations which comprise the active ingredient of the formula I together with or without a solid or liquid additive are prepared in a manner known per se, for example by intimately mixing and/or grinding the active ingredient with extenders, such as solvents, solid carders and, if desired, surface-active compounds (surfactants).

The following are suitable as solvents: aromatic hydrocarbons, preferably the fractions $C_8$ to $C_{12}$, such as xylene mixtures or substituted naphthalenes, phthalic esters, such as dibutyl phthalate or dioctyl phthalate, aliphatic hydrocarbons, such as cyclohexane or paraffins, alcohols and glycols as well as their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, as well as free or epoxidized vegetable oils, such as epoxidized coconut oil or soya oil, and water.

As a rule, solid carders which are used, for example for dusts and dispersible powders, are ground natural minerals, such as calcite, talc, kaolin, montmorillonite or attapulgite. To improve the physical properties, it is also possible to add highly disperse silica or highly disperse absorptive polymers. Suitable particulate, adsorptive carders for granules are porous types, such as pumice, brick grit, sepiolite or bentonite, and suitable non-sorptive carrier materials are, for example, calcite or sand. Moreover, a large number of pregranulated materials of inorganic or organic nature, such as dolomite or comminuted plant residues, may be used.

Depending on the type of the active ingredient of the formula I to be formulated, suitable surface-active compounds are non-ionic, cationic and/or anionic surfactants which have good emulsifying, dispersing and wetting properties. Surfactants are also to be understood as meaning surfactant mixtures.

Suitable anionic surfactants can be either soaps, or water-soluble synthetic surface-active compounds.

Examples which may be mentioned of non-ionic surfactants are nonylphenolpolyethoxyethanols, castor oil polyglycol ether, polypropylene/polyethylene oxide adducts, tributylphenoxypolyethylene-ethanol, polyethylene glycol and octylphenoxypolyethoxyethanol. Other suitable substances are fatty acid esters of polyoxyethylene sorbitan, such as polyoxyethylene sorbitan trioleate.

The cationic surfactants are mainly quaternary ammonium salts which have, as N-substituents, at least one alkyl radical having 8 to 22 C atoms and, as further substituents, lower, free or halogenated alkyl, benzyl or lower hydroxyalkyl radicals.

Other surfactants conventionally used in the art of formulation are known to the expert or can be found in the relevant specialist literature.

As a rule, the agrochemical compositions comprise 0.1 to 99 per cent by weight, in particular 0.1 to 95 per cent by weight, of active ingredient of the formula I, 99.9 to 1 per cent by weight, in particular 99.8 to 5 per cent by weight, of a solid or liquid additive and 0 to 25 per cent by weight, in particular 0.1 to 25 per cent by weight, of a surfactant.

While concentrated compositions are more preferred as commercially available goods, the end consumer uses, as a rule, dilute compositions.

The compositions may also comprise other additives, such as stabilizers, antifoams, viscosity regulators, binders or tackifiers as well as fertilizers or other active ingredients for achieving specific effects.

1. Preparation Examples

Temperatures are given in degrees Celsius. The following abbreviations are used: Ac=acetyl; Et=ethyl; i-Pr=isopropyl; Me=methyl; Ph=phenyl; Pr=n-propyl; Bu=n-butyl; THF= tetrahydrofuran; $Et_2$=diethyl ether; TMP=tetramethylpiperidine; LTMP=lithium-tetramethylpiperidine; RT=room temperature; RM=reaction mixture; i.v.=in vacuo; AcOH=acetic acid; DMF=dimethylformamide; m.p.=melting point. "NMR" is "Nuclear Magnetic Resonance Spectrum". MS=mass spectrum. "%" is "per cent by weight", unless the relevant concentrations are given in a different unit.

Example H-1

Preparation of N,N-diethyl-3-(N',N'-diethylthiocarbamoyloxy)picolinamide:

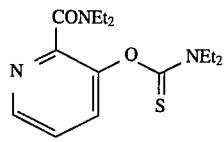

258.3 g (1.33 mol) of 3-hydroxy-N,N-diethylpicolinamide are introduced into 1 l of dimethylpropyleneurea and 213.2 ml (1.53 mol) of triethylamine at 0° C., and 222 g (1.464 mol) of diethylthiocarbamoyl chloride are introduced in the form of a solid. After the reaction mixture has been stirred for 2 hours at 0° C., it is poured into 2 l of water and extracted three times using ethyl acetate, the ethyl acetate phases are washed five times using 500 ml of water in each case, and the combined organic phases are dried over Na₂SO₄ and concentrated in vacuo at 60° C. Recrystallization from Et₂O/hexane gives 341 g (83%) of brown crystals, m.p. 70°–72° C.

Example H-2

Preparation of N,N-diethyl-4-azido-3-(N',N'-diethylthiocarbamoyloxy)picolinamide:

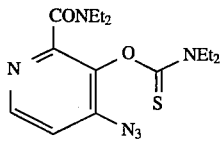

378 ml of n-butyllithium (1.6M in hexane) are added to a solution of 88.2 g (0.624 mol) of 2,2,6,6-tetramethylpiperidine in 1 l of THF at −20° C. under argon and the mixture is stirred at this temperature for 1 hour. The mixture is then cooled to −100° C., and a solution of 104.4 g (0.337 mol) of N,N-diethyl-3-(N',N'-diethylthiocarbamoyloxy)picolinamide in 300 ml of THF is added dropwise in such a way that the temperature does not exceed −90° C. After the mixture has been stirred at −95° C for 1 hour, it is again cooled to −102° C, and a solution of 119.3 g (0.605 mol) of tosyl azide in 200 ml of THF, cooled to −20° C., is added in the course of 30 seconds. After the mixture has been stirred at −80° C. for 15 minutes, 400 ml of a saturated NH₄Cl solution are added, the mixture is heated to 0° C., and the aqueous phase is separated off and washed with 500 ml of diethyl ether and the organic phases are washed once with 200 ml of saturated NH₄Cl solution and twice with in each case 150 ml of saturated NaCl solution, dried over Na₂SO₄ and concentrated in vacuo. The brown oil is taken up in 1.2 l of hexane under hot conditions, the mixture is slowly cooled to 0° C., with stirring, and the solid substance is filtered off and dried. Yield: 109.0 g of beige-brown crystals which are employed directly in the subsequent step.

Example H-3

N,N-diethyl-4-amino-3-(N',N'-diethylcarbamoylthio)picolinamide:

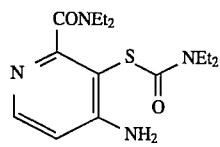

25.0 g (0.66 mol) of NaBH₄ are introduced in portions into a solution of 191.0 g (0.545 mol) of N,N-diethyl-4-azido-3-(N',N'-diethylthiocarbamoyloxy)picolinamide in 1 l of methanol at 8° C. in the course of 2 hours in such a way that the temperature does not exceed 15° C. After the reaction mixture has been stirred for 30 minutes, it is cooled to 8° C., the pH is brought to 7 using approximately 200 ml of 3 N HCl, and most of the methyl alcohol is distilled off in vacuo at 60° C. The residue is taken up in 500 ml of ethyl acetate, the ethyl acetate phase is washed 3× with water, and the organic phase is dried over Na₂SO₄ and concentrated in vacuo at 60° C. The crystalline residue is recrystallized from ethyl acetate/diethyl ether/hexane.

Yield: 141 g (80%) of colourless crystals, m.p. 144°–147° C.

Example H-4

Preparation of N,N-diethyl-7-[1,2,3]thiadiazole[5,4,c]pyridinecarboxamide:

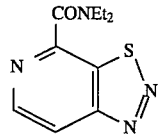

420 ml of acetic acid and then 120 ml of trifluoroacetic acid (TFA) are introduced into a solution of 161.3 g (0.497 mol) of N,N-diethyl-4-amino-3-(N',N'-diethylcarbamoylthio)picolinamide in 3 l of dimethoxyethane (DME) at −25° C. 160 ml (1.2 mol) of isoamyl nitrite are subsequently added dropwise at −25° to −20° C. in the course of 10 minutes and the reaction mixture is stirred overnight, during which process the temperature rises from 0° C. to 12° C. The reaction mixture is concentrated in vacuo at 60° C., the residue is taken up in 1.5 l of ethyl acetate and 2 l of water, the ethyl acetate phase is brought to pH 7 using approximately 90 g of NaHCO₃, the aqueous phase is separated off and washed 2× using ethyl acetate, and the combined organic phases are washed 2× with water, dried over Na₂SO₄ and concentrated in vacuo at 60° C. The residue is taken up in diethyl ether, filtered over 500 g of silica gel and recrystallized from diethyl ether/hexane.

Yield: 100 g (85%) of colourless crystals, m.p. 97°–99° C.

Example H5

Preparation of 7-[1,2,3]thiadiazole[5,4,c]pyridine carboxylic acid:

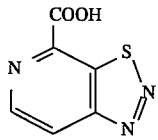

100 g (0.423 mol) of N,N-diethyl-7-[1,2,3]thiadiazole[4,5-c]pyridinecarboxamide are refluxed in 500 ml of acetic acid and 500 ml of concentrated hydrochloric acid for 5 hours. The acetic acid is subsequently removed in vacuo at 60° C., the residue is treated with 1.5 l of water and cooled to 0° C., and the yellowish crystals are filtered off with suction, washed with ice water and dried in vacuo at 60° C.

Yield: 70 g (91%) of yellowish crystals, m.p. 174°–175° C. (decomposition).

Example H-6

Preparation of methyl 7-[1,2,3]thiadiazole[5,4-c]pyridinecarboxylate:

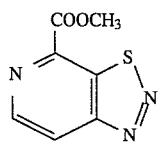

32 ml (0.441 mol) of thionyl chloride are introduced into a suspension of 27 g (0.149 mol) of 7-[1,2,3]thiadiazole[4,5-c]pyridinecarboxylic acid in 250 ml of benzene at approximately 25° C., the mixture is refluxed, and 0.1 ml of dimethylformamide (DMF) are added. After the mixture has been refluxed for 2 hours, a further 16 ml of thionyl chloride are added, and the mixture is refluxed for a further hour. The reaction mixture is then concentrated in vacuo at 60° C.; 29.9 g of violet crystals are obtained. These crystals are taken up in 200 ml of methanol, 13.3 ml of pyridine are added, and the mixture is stirred for 2 hours. The reaction mixture is evaporated in vacuo at 60° C., and the residue is taken up in ethyl acetate and washed with water, during which process some of the product precipitates. After the clear solution has been heated to 60° C., it is treated with active charcoal and filtered, and the filtrate is then concentrated in vacuo at 60° C. and the residue recrystallized from diethyl ether.

Yield: 26.6 g (92%) of pink crystals, m.p. 180°–182° C.

Example H-7

Preparation of 2-fluoro-3-dihydroxyborylpyridine:

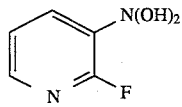

800 ml (1.28 mol) of n-BuLi (1.6M in hexane) are added to a solution of 188 ml (1.32 mol) of TMP in 1,000 ml of THF at −78° C. under argon. After the mixture has been stirred for 45 minutes at this temperature, 120.4 g (1.24 mol) of 2-fluoropyridine in 200 ml of THF are added in the course of 3 minutes. After the mixture has been stirred for 4 hours at −78° C., a solution of 128.8 g (1.24 mol) of trimethyl borate in 200 ml of THF is added dropwise in the course of 20 minutes. Then, 200 ml of a 1:1 mixture of water/THF is added at 25° C., and 256 ml of concentrated HCl are added dropwise, with ice-cooling. The organic phase is separated off, and the aqueous phase is washed twice using Et₂O, filtered and concentrated in vacuo. Crude yield 148.2 g.

Example H-8

Preparation of 2-fluoro-3-hydroxy-pyridine:

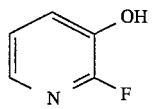

30 g (560 mmol) of NH₄Cl are added to a solution of 61.1 g (434 mmol) of 2-fluoro-3-dihydroxyborylpyridine in 500 ml of water. Then, 300 ml of a 30% H₂O₂ solution are added dropwise in the course of 30 minutes, and the temperature is kept below 25° C. by means of ice-cooling; the mixture is stirred overnight at room temperature and then cooled to 0° C., the solid is filtered off with suction, and the aqueous phase is extracted 3 times using ethyl acetate, and the combined organic phases are dried over Na₂SO₄ and concentrated in vacuo at 60° C. Yield 44.5 g of colourless crystals of m.p. 131°–133° C.

Example H-9

Preparation of 3-diethylthiocarbamoyloxy-2-fluoropyridine:

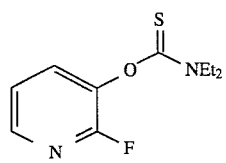

36.2 g (358 mmol) of triethylamine and 54.3 g (358 mmol) of diethylthiocarbamoyl chloride are added in succession to a suspension of 36.7 g (325 mmol) of 2-fluoro-3-hydroxypyridine in 150 ml of toluene at room temperature, and the reaction mixture is heated at 75° C. After the reaction mixture has been stirred at this temperature for 1 hour, it is cooled to room temperature, diluted with ethyl acetate, washed 3 times with water, dried over Na₂SO₄ and concentrated in vacuo at 60° C.; 80 g of brown oil which, after recrystallization from Et₂O/hexane, gave 64.2 g (86%) of brown crystals of m.p. 52°–54° C.

Example H-10

Preparation of N,N-diethyl-3-(diethylthiocarbamoyloxy)-2-fluoronicotinamide:

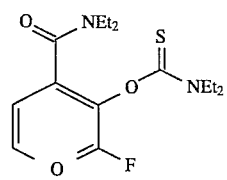

250 ml (400 mmol) of n-BuLi (1.6M in hexane) are added to a solution of 57.9 g (410 mmol) of TMP in 750 ml of THF at −10° C. After the mixture has been stirred for 1 hour at −10° C., a solution of 64 g (280 mmol) of 3-diethylthiocarbamoyloxy-2-fluoropyridine in 200 ml of THF is added dropwise at −78° C. in the course of 30 minutes. After the mixture has been stirred for 1 hour at −78° C., 81.4 g (600 mmol) of diethylcarbamoyl chloride are added in the course of 1 minute, the mixture is stirred at −78° C. for 2 hours and heated to −20° C., 130 ml of 3N HCl are added, and the mixture is diluted with 1 l of water and brought to pH 7. The organic phase is washed 3 times with water. The combined aqueous phases are extracted twice using Et₂O, and the combined organic phases are washed twice with water, dried over Na₂SO₄ and concentrated in vacuo at 60° C.: 116 g of a brown oil. Chromatography (ethyl acetate/hexane 1:1) gives 60 g (65%) of beige crystals of m.p. 87°–92° C.

Example H-11

Preparation of N,N-diethyl-3(diethylcarbamoylthio)-2-fluoronicotinamide:

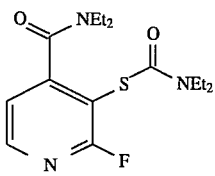

60 g (183 mmol) of N,N-diethyl-3-(diethylthiocarbamoyloxy)-2-fluoronicotinamide are heated in 500 g of diphenyl ether at 200° C. for 8 hours under argon. The diphenyl ether is then distilled off at 120° C./0.05 bar and the residue is chromatographed on silica gel using Et$_2$O. The subsequent recrystallization gives 40.5 g (68%) of beige crystals of m.p. 87°–88° C.

Example H-12

Preparation of N,N-diethyl-2-amino-3-(diethylcarbamoylthio)nicotinamide:

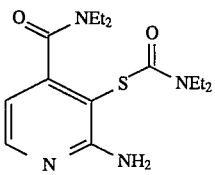

43 g of ammonia are injected into an autoclave with a solution of 40.2 g (122 mmol) of N,N-diethyl-3-(diethylcarbamoylthio)-2-fluoronicotinamide in 350 g of methanol, and the mixture is heated at 100° C. for 10 hours. It is then concentrated in vacuo and chromatographed on silica gel using ethyl acetate. Subsequent recrystallization from Et$_2$O/hexane gives 18.7 g (47%) of yellowish crystals.

Example H-13

Preparation of di(2-amino)nicotinyl diethylamido-3,3'-disulfide:

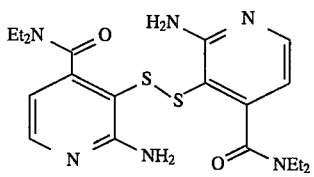

8.4 g (66 mmol) of nitrosylsulfuric acid are added to a solution of 18.0 g (55.0 mmol) of N,N-diethyl-2-amino-3-(diethylcarbamoylthio)nicotinamide in concentrated sulfuric acid and the mixture is stirred for 2 hours at 50° C. The mixture is then poured, at room temperature, into a solution of 96 g of NaOH in 550 ml of ice-water, brought to pH 7–8 using NaHCO$_3$, saturated with NaCl and extracted 6 times with ethyl acetate. The combined organic extracts are dried over Na$_2$SO$_4$ and concentrated in vacuo at 60° C. Recrystallization of the brown resin from ethyl acetate/hexane gives 13.9 g (47%) of yellow crystals of m.p. 176°/179° C.

Example H-14

Preparation of N,N-diethyl-7-[1,2,3]thiadiazole[4,5-b]pyridinecarboxamide N-oxide:

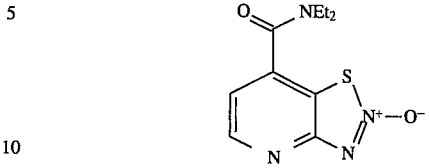

10.5 g (92 mmol) of trifluoroacetic acid are added to a solution of 13.8 g (30.8 mmol) of di-(2-amino-4-diethylcarbamoylpyridyl) 3,3'-disulfide in 200 ml of dimethoxyethane (DME) at room temperature, the mixture is heated at 50° C., and a solution of 8.67 g (74 mmol) of isoamyl nitrite in 50 ml DME is added dropwise in the course of 1 hour. After the reaction mixture has been stirred for 30 minutes at 50° C., it is cooled to 0° C., a seed crystal is added, and the mixture is subsequently filtered. Washing of the solids gives 4 g (26%) of beige crystals.

Example H-15

Preparation of N,N-diethyl-7-[1,2,3]thiadiazole[4,5-b]pyridinecarboxamide:

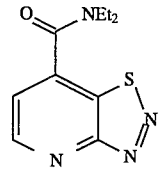

A solution of 2.94 g (18 mmol) of tris(dimethylamino)phosphine is added dropwise to a solution of 4.57 g (18 mmol) of iodine in 45 ml of acetonitrile in the course of 15 minutes. Then, 3.0 g (11.9 mmol) of N,N-diethyl-7-[1,2,3]thiadiazole[4,5-b]pyridinecarboxamide N-oxide are added and the mixture is refluxed for 10 hours. After the mixture has cooled to room temperature, it is poured into a dilute sodium thiosulfate solution and extracted 3 times using ethyl acetate. The combined organic phases are dried over Na$_2$SO$_4$ and concentrated in vacuo at 60° C. After chromatography on silica gel using Et$_2$O, 1.8 g (66%) of yellowish crystals of m.p. 186°–188° C. are obtained.

Example H-16

Preparation of 7-[1,2,3]thiadiazole[4,5-b]pyridinecarboxylic acid:

2.3 g (9.73 mmol) of N,N-diethyl-7-[1,2,3]thiadiazole[4,5-b]pyridinecarboxamide are refluxed in a mixture of 10 ml of AcOH and 10 ml of concentrated HCl for 5 hours. The mixture is then concentrated almost to dryness in vacuo at 60° C., the product is suspended in 75 ml of H$_2$O, the suspension is cooled to 0° C., and the solid is filtered off with suction and dried in vacuo at 60° C.: 1.45 g (82%) of pale brown powder of m.p. 230° C. (decomposition).

Example H-17
Preparation of Methyl 7-[1,2,3]thiadiazole[4,5-b]pyridinecarboxylate:

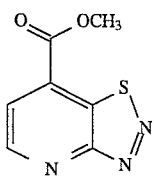

0.93 g (7.9 mmol) of thionyl chloride and 1 drop of DMF are added to a suspension of 0.57 g (3.1 mmol) of 7-[1,2,3]thiadiazole[4,5-b]pyridinecarboxylic acid in 20 ml of benzene. After the mixture had been refluxed for 1 hour, a further 0.93 g (7.8 mmol) of thionyl chloride is added and the mixture is refluxed for a further 2.5 hours. It is then concentrated in vacuo at 60° C., the product is taken up in 50 ml of methanol, and the mixture is stirred until a clear solution is formed. Thereupon, the mixture is concentrated in vacuo at 60° C., the residue is taken up in ethyl acetate, and the mixture is filtered using 25 g of silica gel and the filtrate reconcentrated and dried: 0.6 g (99%) of yellowish crystals of m.p. 145°–147° C.

The compounds given in the tables which follow can be prepared analogously to the procedure described in the above examples or by one of the other processes described hereinabove:

TABLE 1

| Comp. No. | A | Physical data |
| --- | --- | --- |
| 1.1 | OH | m.p. 174–175° C. |
| 1.2 | O⁻Na⁺ | |
| 1.3 | O—Me | m.p. 178–180° C. |
| 1.4 | O—Et | m.p. 104–106° C. |
| 1.5 | O—Pr | m.p. 76–77° C. |
| 1.6 | O-i-Pr | m.p. 65–67° C. |
| 1.7 | O-Allyl | m.p. 61–62° C. |
| 1.8 | O—Bu | $n_D$ = 1.5678 |
| 1.9 | O-s-Bu | |
| 1.10 | O-t-Bu | |
| 1.11 | O-pentyl | |
| 1.12 | O—CH₂-cyclopropyl | m.p. 88–90° C. |
| 1.13 | O—CH₂CH₂-cyclopropyl | |
| 1.14 | O—CH₂CH₂CH₂—OH | |
| 1.15 | O—CH₂—CH(OH)—CH₂OH | |
| 1.16 | O—CH₂CC(Me)₃ (with C=O) | |
| 1.17 | O—CH₂CF₃ | m.p. 89–90° C. |
| 1.18 | —OCH₂CH₂OMe | m.p. 64–72° C. |
| 1.19 | —OCH₂CH₂OPh | m.p. 89–91° C. |
| 1.20 | O-phenyl | m.p. 166–167° C. |
| 1.21 | O-(2-chlorophenyl) | |
| 1.22 | O-(4-tert-butylphenyl) | |
| 1.23 | O-(4-methylphenyl) | |
| 1.24 | O-(3-trifluoromethylphenyl) | |
| 1.25 | O-(3-nitrophenyl) | |
| 1.26 | O-naphthyl | m.p. 167–169° C. |
| 1.27 | O-benzyl | m.p. 103–105° C. |
| 1.28 | O-(1-phenylethyl) | |
| 1.29 | O-(2-phenylethyl) | |
| 1.30 | O-(2-fluorobenzyl) | m.p. 103–105° C. |
| 1.31 | O-(3-fluorobenzyl) | m.p. 130–131° C. |
| 1.32 | O-(4-fluorobenzyl) | |
| 1.33 | O-(pentafluorobenzyl) | |
| 1.34 | O-(3-methoxybenzyl) | m.p. 135–136° C. |
| 1.35 | O-(4-chlorobenzyl) | m.p. 160–162° C. |
| 1.36 | O-(3,4-dichlorobenzyl) | m.p. 149–151° C. |
| 1.37 | O-(4-methylbenzyl) | m.p. 126–127° C. |
| 1.38 | O-(4-methoxybenzyl) | m.p. 118–119° C. |
| 1.39 | O-(2-nitrobenzyl) | |
| 1.40 | O-(2-pyridylmethyl) | m.p. 113–115° C. |
| 1.41 | O-(3-pyridylmethyl) | m.p. 162–163° C. |
| 1.42 | O-(4-pyridylmethyl) | |
| 1.43 | O-(2-furanylmethyl) | |
| 1.44 | O—N=cyclohexylidene | |
| 1.45 | O—N=(4-t-Bu-cyclohexylidene) | |
| 1.46 | S—Me | m.p. 180–181° C. |
| 1.47 | S—Et | m.p. 80–82° C. |
| 1.48 | S—Pr | m.p. 65–66° C. |
| 1.49 | S-i-Pr | m.p. 103–104° C. |
| 1.50 | S-benzyl | m.p. 118–119° C. |
| 1.51 | S-(2-pyridyl) | |
| 1.52 | S-(2-furanyl)methyl | |
| 1.53 | S-allyl | m.p. 80–82° C. |
| 1.54 | O-(2-chloroprop-2-enyl) | m.p. 71–72° C. |
| 1.55 | O-i-prop-2-enyl | m.p. 57–59° C. |
| 1.56 | O-geranyl | m.p. 43–44° C. |
| 1.57 | O-(4-tert-butylbenzyl) | m.p. 124–126° C. |
| 1.58 | O-(4-trifluoromethoxybenzyl) | m.p. 107–109° C. |
| 1.59 | O-(3-nitrobenzyl) | m.p. 171–172° C. |
| 1.60 | O-(2-thiophenylmethyl) | m.p. 94–95° C. |
| 1.61 | S-phenyl | m.p. 166–167° C. |

TABLE 2

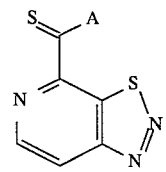

| Comp. No. | A | Physical data |
| --- | --- | --- |
| 2.1 | O—Me | |
| 2.2 | O—Et | |
| 2.3 | O—(4-chlorobenzyl) | |
| 2.4 | S—Me | |
| 2.5 | S—Et | |

TABLE 2-continued

| Comp. No. | A | Physical data |
|---|---|---|
| 2.6 | S—Pr | |
| 2.7 | S-i-Pr | |
| 2.8 | O-Pentyl | Oil |

TABLE 2-continued

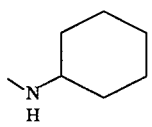

| Comp. No. | A | Physical data |
|---|---|---|
| 2.9 | NH—Me | m.p. 180–181° C. |
| 2.10 | NH—Et | m.p. 162–165° C. |

TABLE 3

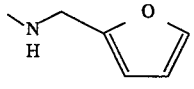

| Comp. No. | $R_3$ | $R_4$ | Physical data |
|---|---|---|---|
| 3.1 | H | H | m.p. >250° C. |
| 3.2 | H | Me | |
| 3.3 | Me | Me | |
| 3.4 | H | Et | |
| 3.5 | Et | Et | m.p. 97–99° C. |
| 3.6 | H | Pr | |
| 3.7 | H | OH | m.p. 233–234° C. decomp. |
| 3.8 | H | $OCH_3$ | |
| 3.9 | H | $CH_2OH$ | m.p. >250° C. |
| 3.10 | H | $CH_2OCH_3$ | m.p. 138–140° C. |
| 3.11 | H | $CH_2OC(=O)CH_3$ | m.p. 130–132° C. |
| 3.12 | H | $CH_2N(CH_3)CHO$ | m.p. 169–171° C. |
| 3.13 | H | $CH_2COOH$ | |
| 3.14 | H | $CH_2COOCH_3$ | |
| 3.15 | H | $CH(CH_3)COOCH_3$ | m.p. 78–79° C. |
| 3.16 | H | $CH(CH_3)COOCH_2Ph$ | |
| 3.17 | H | $CH(i\text{-}Pr)COOCH_3$ | Resin, NMR |
| 3.18 | H | $CH(i\text{-}Pr)COOCH_2Ph$ | Resin |
| 3.19 | H | $CH(CH_2C(CH_3)_2)COOCH_3$ | m.p. 91–92° C. |
| 3.20 | H | $CH(CH(CH_3)C_2H_5)COOCH_3$ | m.p. 50–54° C. |
| 3.21 | H | $N=C(CH_3)_2$ | |
| 3.22 | H | $N=CHCCl_3$ | |
| 3.23 | H | 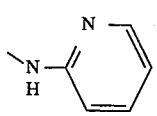 | |
| 3.24 | H | | |
| 3.25 | H | $N(CH_3)_2$ | |
| 3.26 | H | $NHCH(CH_3)_2$ | |
| 3.27 | H | $NHCH(C_2H_5)_2$ | |
| 3.28 | H | NHPh | |
| 3.29 | H | $NHCH_2Ph$ | |
| 3.30 | H | NH-2,4,6-trichlorophenyl | m.p. 234–236° C. |
| 3.31 | H | | |

TABLE 3-continued

| Comp. No. | R₃ | R₄ | Physical data |
|---|---|---|---|
| 3.32 | H | 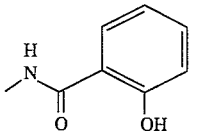 | m.p. >250° C. |
| 3.33 | H | propargyl | m.p. 159–160° C. |
| 3.34 | H | CH₂COOCH₂Ph | m.p. 106–109° C. |
| 3.35 | H | CH(CH₃)COO(2-F-benzyl) | m.p. 99–100° C. |
| 3.36 | H | CH(CH₂C(CH₃)₂)COO(2-F-benzyl) | m.p. 66–69° C. |
| 3.37 | H | benzyl | m.p. 177–179° C. |
| 3.38 | H | 2-chlorobenzyl | m.p. 182–183° C. |
| 3.39 | H | 3,4-dimethoxybenzyl | m.p. 165–166° C. |
| 3.40 | H | 2-(trifluoromethyl)benzyl | m.p. 163–164° C. |
| 3.41 | H | 4-carboxybenzyl | m.p. >260° C. |
| 3.42 | H | 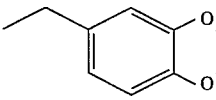 | m.p. 194–195° C. |
| 3.43 | H | 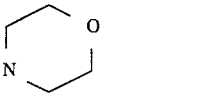 | m.p. 207–208° C. |
| 3.44 | H |  | m.p. 106–107° C. |
| 3.45 | H |  | m.p. 146–148° |

TABLE 4

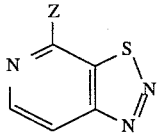

| Comp. No. | Z | Physical data |
|---|---|---|
| 4.1 | CN | m.p. 72–74° C. |
| 4.2 | CHO | m.p. 96–98° C. |
| 4.3 | CH₂—OCOCH₃ | m.p. 108–109° C. |
| 4.4 | CH₂—O—CO—CH₂—Ph | m.p. 106–108° C. |
| 4.5 | CH₂OH | m.p. 154–156° C. |
| 4.6 | CH=N—OCH₂ | |
| 4.7 | CF₃ | |
| 4.8 | CHF₂ | |
| 4.9 | CCl₃ | |
| 4.10 | CH₂—OCH₃ | |
| 4.11 | CH(OCH₃)₂ | |
| 4.12 | CH=N—CH₃ | |
| 4.13 | CH=N—NH—Ph | |

TABLE 5

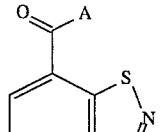

| Comp. No. | A | Physical data |
|---|---|---|
| 5.1 | OH | m.p. 230° C. decomp. |
| 5.2 | O—Me | m.p. 145–147° C. |
| 5.3 | O—Et | |
| 5.4 | O-benzyl | |
| 5.5 | S—Me | |
| 5.6 | S—Et | |
| 5.7 | S-benzyl | |

TABLE 6

| Comp. No. | $R_3$ | $R_4$ | Physical data |
|---|---|---|---|
| 6.1 | H | H | |
| 6.2 | H | Me | |
| 6.3 | H | Et | |
| 6.4 | H | OH | |
| 6.5 | H | $CH(i-Pr)COOCH_3$ | |

TABLE 7

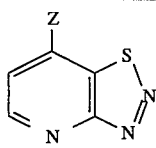

| Comp. No. | Z | Physical data |
|---|---|---|
| 7.1 | CN | |
| 7.2 | CHO | |
| 7.3 | $CH_2-OCOCH_3$ | |
| 7.4 | $CH_2-O-CO-CH_2-Ph$ | |
| 7.5 | $CH_2OH$ | |
| 7.6 | $CH=N-OCH_2$ | |
| 7.7 | $CF_3$ | |
| 7.8 | $CHF_2$ | |
| 7.9 | $CCl_3$ | |
| 7.10 | $CH_2-OCH_3$ | |
| 7.11 | $CH(OCH_3)_2$ | |
| 7.12 | $CH=N-CH_3$ | |
| 7.13 | $CH=N-NH-Ph$ | |

2. Formulation examples for active ingredients of the tables (%=per cent by weight)

| 2.1 Wettable powders | a) | b) | c) |
|---|---|---|---|
| Active ingredient from the tables | 25% | 50% | 75% |
| Sodium lignosulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 mol of ethylene oxide) | — | 2% | — |
| Highly-disperse silica | 5% | 10% | 10% |
| Kaolin | 62% | 27% | — |

The active ingredient is mixed with the additives and the mixture is ground in a suitable mill until homogeneous. This gives wettable powders which can be diluted with water to give suspensions of any desired concentration.

| 2.2 Emulsion concentrate | |
|---|---|
| Active ingredient from the tables | 10% |
| Octylphenol polyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired dilution can be prepared from this concentrate by diluting it with water.

| 2.3 Dusts | a) | b) |
|---|---|---|
| Active ingredient from the tables | 5% | 8% |
| Talc | 95% | — |
| Kaolin | — | 92% |

Ready-for-use dusts are obtained by mixing the active ingredient with the carriers and grinding the mixture in a suitable mill.

| 2.4 Extruder granules | |
|---|---|
| Active ingredient from the tables | 10% |
| Sodium lignosulfonate | 2% |
| Carboxymethylcellulose | 1% |
| Kaolin | 87% |

The active ingredient is mixed with the additives, and the mixture is ground and moistened with water. This mixture is extruded and subsequently dried in a stream of air.

| 2.5 Coated granules | |
|---|---|
| Active ingredient from the tables | 3% |
| Polyethylene glycol (MW 200) | 3% |
| Kaolin | 94% |
| (MW = molecular weight) | |

In a mixer, the finely ground active ingredient is applied uniformly to the kaolin which has been moistened with polyethylene glycol. In this manner, dust-free coated granules are obtained.

| 2.6 Suspension concentrate | |
|---|---|
| Active ingredient from the tables | 40% |
| Ethylene glycol | 10% |
| Nonylphenol polyethylene glycol ether (15 mol of ethylene oxide) | 6% |
| Sodium lignosulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. This gives a suspension concentrate from which suspensions of any desired dilution can be prepared by diluting it with water.

3. Biological Examples

Example 3.1

Efficacy against *Colletotrichum lagenarium* on *Cucumis sativus* L.

a) Cucumber plants are grown for 2 weeks and then sprayed with a spray mixture prepared with a wettable powder of the active ingredient (concentration: 200 ppm). After 72 hours, the plants are inoculated with a spore suspension ($1.0 \cdot 10^5$ spores/ml) of the fungus and incubated for 30 hours at high atmospheric humidity and a temperature of 23° C. Incubation is then continued at normal atmospheric humidity and 22° C. to 23° C. The protective action is assessed 7–8 days after infection on the basis of the fungus infestation.

b) Cucumber plants are grown for 2 weeks and then treated by soil application using a spray mixture prepared with a wettable powder of the active ingredient (concentration: 20 ppm relative to the soil volume). After 72 hours, the plants are inoculated with a spore suspension (1.5·10⁵ spores/ml) of the fungus and incubated for 30 hours at high atmospheric humidity and a temperature of 23° C. Incubation is then continued at normal atmospheric humidity and 22° C.

The protective action is assessed 7–8 days after infection on the basis of the fungus infestation.

Compounds from the tables are very effective in tests (a) and (b) and reduce fungus infestation to 0 to 20%. In contrast, untreated but infected control plants show Colletotrichum infestation of 100%.

Example 3.2

Efficacy against Phytophthora infestans on tomato plants a) Tomato plants are grown for 3 weeks and then sprayed with a spray mixture prepared with a wettable powder of the active ingredient (0.02% of active ingredient). After 72 hours, the treated plants are inoculated with a sporangia suspension of the fungus. The fungus infestation is assessed after incubation of the inoculated plants for 5 days at 90–100% relative atmospheric humidity and 20° C.

Compounds from the tables are very effective in the tests and reduce fungus infestation to 0 to 20%. In contrast, untreated, but inoculated control plants show 100% Phytophthora infestation.

Example 3.3

Efficacy against *Pyficularia oryzae* on rice plants

A spray mixture prepared with a wettable powder of the active ingredient is poured on to 2-week-old rice plants (0.006% of active ingredient relative to the soil volume). Thereupon, the pots are filled with water so that the lowest parts of the rice plant stalks are submerged. After 96 hours, the treated rice plants are inoculated with a conidia suspension of the fungus. The fungus infestation is assessed after incubation of the inoculated plants for 5 days at 95–100% relative atmospheric humidity and approximately 24° C. In comparison with untreated control plants (100% infestation), rice plants which have been treated with a spray mixture which comprises a compound from the tables as active ingredient, only show approximately 50% fungus infestation.

Example 3.4

Efficacy against *Peronospora tabacina* on tobacco plants a) Foliar application

Tobacco plants (8 weeks old) are sprayed with a formulated solution of the active ingredient (concentration: 0.02% of active ingredient). Four days after the treatment, the plants are inoculated with a sporangia suspension of *Peronospora tabacina* (100 sporangia/ml), stored for 20 hours in the dark at 25° C. and high atmospheric humidity and then further incubated in a normal day/night sequence. The symptoms in the tests are assessed on the basis of the leaf area infested with fungus.

The control plants show an infestation of 90 to 100%. Plants which have been treated with compounds from the tables show an infestation of 0–30%.

Example 3.5

Efficacy against *Erysiphe graminis* on wheat

Protective action 18-day-old wheat plants are sprayed with a formulated solution of the active ingredient (0.02% of active ingredient). Immediately after the treatment, the plants are incubated under cylinders. After 24 hours, the plants are covered. After a further 3 days, the treated plants are cut above the primary leaf. The primary leaves are arranged horizontally and inoculated with *Erysiphe graminis* spores in a dusting chamber (spore density: 0.2 mg per m²). The test is carried out in a controlled-environment cabinet under 12 hours of light (288 KLux), 20° C., and 12 hours of darkness, 18° C.

The infestation is assessed 9 and 13 days after inoculation.

In the tests, compounds from the tables are very effective and reduce fungus infestation to 0 to 20%. In contrast, untreated, but inoculated control plants show 100% Erysiphe infestation.

Example 3.6

Efficacy against *Puccinia graminis* on wheat 6-day-old wheat plants are sprayed with a formulated solution of the active ingredient (0.02% of active ingredient). After 24 hours, the plants are inoculated with a uredospore suspension (100,000 per ml). Infestation is determined 10 days later. In the tests, compounds from the tables are very effective and reduce fungus infestation to 0 to 20%. In contrast, untreated, but infected control plants show 100% Puccinia infestation.

What is claimed is:

1. A compound of the formula I (I)

in which a) X is CH and Y is N; or b) X is N and Y is CH; and in which

Z is a $C_1$ group to which them are bonded 1–3 halogen atoms or 1–3 substituted or unsubstituted hetero atoms O, S and/or N; in free form or in salt form.

2. A compound of the formula I according to claim 1 in which:

Z is CN, CO—A, CS—A, CH=U, $CH_2$—V, CH(—V)$_2$ or C(—V)$_3$; and in which furthermore the remaining substituents are as follows:

A is $OR_2$, $SR_2$, $N(R_3)R_4$, $N(R_5)$—$OR_6$, O—N(=C)$_n$($R_7$)$R_8$ or N($R_9$)—N(=C)$_n$($R_7$)$R_8$;

U is O, $NR_{10}$, N—$OR_6$ or N—N(=C)$_n$($R_7$)$R_8$;

V is halogen, hydroxyl, $C_1$–$C_4$alkoxy, $C_1$–$C_4$acyloxy benzoyloxy, benzyloxy, or two V together with the carbon atom to which they are bonded are a cyclic acetal group;

n is 0 or 1;

$R_2$ to $R_{10}$ are hydrogen, a substituted or unsubstituted open-chain, saturated or unsaturated hydrocarbon radical having up to 8 carbon atoms, a substituted or unsubstituted cyclic, saturated or unsaturated hydrocarbon radical having up to 10 carbon atoms, substituted or unsubstituted benzyl or phenethyl, a substituted or unsubstituted acyl group having up to 8 carbon atoms, a substituted or unsubstituted benzoyl group, or a substituted or unsubstituted heterocyclyl radical; or $R_3$ and $R_4$ together with the nitrogen atom to which they are bonded are a 5- or 6-membered, substituted or unsubstituted heterocycle; or $R_7$ and $R_8$ together with the atom to which they are bonded are a 5- or 6-membered carbocyclic or heterocyclic ring, the abovementioned rings being unsubstituted or substituted; in free form or in salt form.

3. A compound of the formula I according to claim 2, in which:

$R_2$ and $R_3$ are hydrogen, $C_1$–$C_8$alkyl which is unsubstituted or substituted by 1–5 halogen atoms, $C_3$–$C_6$cycloalkyl, $C_1$–$C_4$alkoxy, phenoxy, hydroxyl, nitro, cyano, $C_1$–$C_4$alkanoyl, benzoyl, carboxyl, $C_1$–$C_4$alkoxycarbonyl, benzyloxycarbonyl, $C_1$–$C_4$acyloxy, benzoyloxy, $C_1$–$C_4$dialkylamino or heterocyclyl, $C_3$–$C_6$alkenyl which is unsubstituted or substituted by 1–5 halogen atoms, or are $C_3$–$C_6$alkynyl, $C_3$–$C_6$cycloalkyl, phenyl, benzyl or phenethyl, the phenyl rings of these compounds being unsubstituted or mono- to trisubstituted by halogen, hydroxyl, $C_1$–$C_4$alkyl, halo-$C_1$–$C_2$alkyl, $C_1$–$C_2$alkoxy, halo-$C_1$–$C_2$-alkoxy or nitro, naphthyl, $C_1$–$C_4$alkanoyl, benzoyl, or are heterocyclyl which is unsubstituted or mono- to trisubstituted by identical or different substituents from the series consisting of halogen, $C_1$–$C_2$alkyl, halomethyl or nitro;

$R_4$ is hydrogen, $C_1$–$C_6$alkyl, $C_3$–$C_6$alkenyl, $C_3$–$C_6$alkynyl, $C_3$–$C_6$cycloalkyl, phenyl or benzyl, the phenyl rings of these compounds being unsubstituted or mono- to disubstituted by halogen, hydroxyl, $C_1$–$C_2$alkyl, $C_1$–$C_2$alkoxy, halomethyl or nitro; or $R_3$ and $R_4$ together with the nitrogen atom to which they are bonded are a 5- or 6-membered heterocycle which is unsubstituted or mono- to trisubstituted by $C_1$–$C_2$alkyl; $R_5$, $R_6$, $R_7$, $R_8$, $R_9$ and $R_{10}$ independently of one another are hydrogen, $C_1$–$C_6$alkyl, $C_3$–$C_6$alkenyl, $C_3$–$C_6$alkynyl, $C_3$–$C_6$cycloalkyl, phenyl or benzyl, the phenyl rings of these compounds being unsubstituted or mono- to disubstituted by halogen, hydroxyl, $C_1$–$C_2$alkyl, $C_1$–$C_2$alkoxy, halo-$C_1$–$C_2$alkyl or nitro; or $R_7$ and $R_8$ together with the atom to which they are bonded are a 5- to 7-membered carbocyclic or heterocyclic ring, the abovementioned rings being unsubstituted or mono- to trisubstituted by identical or different substituents from the series consisting of halogen, $C_1$–$C_2$alkyl, halo-$C_1$–$C_2$alkyl or nitro.

4. A compound of the formula I according to claim 3 in which:

$R_2$ and $R_3$ are hydrogen, $C_1$–$C_5$alkyl which is unsubstituted or substituted by 1–3 halogen atoms, $C_3$–$C_6$cycloalkyl, $C_1$–$C_2$alkoxy, phenoxy, hydroxyl, nitro, cyano, $C_1$–$C_2$alkanoyl, benzoyl, carboxyl, $C_1$–$C_4$alkoxycarbonyl, benzyloxycarbonyl, $C_1$–$C_2$acyloxy, benzoyloxy, $C_1$–$C_4$dialkylamino or heterocyclyl or $C_3$–$C_4$alkenyl which is unsubstituted or substituted by 1–3 halogen atoms, $C_3$–$C_4$alkynyl, $C_3$–$C_6$cycloalkyl, phenyl, benzyl or phenethyl, the phenyl rings of these compounds being unsubstituted or mono- to disubstituted by halogen, hydroxyl, $C_1$–$C_4$alkyl, halo-$C_1$–$C_2$alkyl, $C_1$–$C_2$alkoxy, halo-$C_1$–$C_2$alkoxy or by nitro, or are naphthyl or heterocyclyl, unsubstituted or mono- to disubstituted by identical or different substituents from the series consisting of halogen, $C_1$–$C_2$alkyl, halomethyl or nitro;

$R_4$ is hydrogen, $C_1$–$C_4$alkyl, $C_3$–$C_4$alkenyl, $C_3$–$C_4$alkynyl, $C_3$–$C_6$cycloalkyl, phenyl or benzyl;

$R_3$ and $R_4$ together with the nitrogen atom to which they are bonded are pyrrolidine, piperidine, morpholine or dimethylmorpholine;

$R_5$, $R_6$, $R_7$, $R_8$, $R_9$ and $R_{10}$ independently of one another are hydrogen, $C_{1-C4}$alkyl, $C_3$–$C_4$alkenyl, $C_3$–$C_4$alkynyl, $C_3$–$C_6$cycloalkyl, phenyl or benzyl, the phenyl rings of these compounds being unsubstituted or mono- to disubstituted by halogen, hydroxyl, $C_1$–$C_2$alkyl, $C_1$–$C_2$alkoxy, halomethyl or nitro; or $R_7$ and $R_8$ together with the atom to which they are bonded are a 5- to 7-membered carbocyclic or heterocyclic ring, the abovementioned rings being unsubstituted or mono- to disubstituted by identical or different substituents from the series consisting of halogen, methyl, halomethyl or nitro.

5. A compound of the formula I according to claim 2, in which:

Z is CO—A; and

A is $OR_2$, $SR_2$, $N(R_3)R_4$, $N(R_5)$—$OR_6$, O—$N(=C)_n(R_7)R_8$ or $N(R_9)$—$N(-C)_n(R_7)R_8$.

6. A compound of the formula I according to claim 5, in which:

Z is CO—A; and

A is $OR_2$ or $SR_2$.

7. A compound of the formula I according to claim 6, in which:

$R_2$ is hydrogen, $C_1$–$C_5$alkyl which is unsubstituted or substituted by 1–3 halogen atoms, $C_3$–$C_6$cycloalkyl, $C_1$–$C_2$alkoxy, phenoxy, hydroxyl, nitro, cyano, $C_1$–$C_2$alkanoyl, benzoyl, carboxyl, $C_1$–$C_4$alkoxycarbonyl benzyloxycarbonyl, $C_1$–$C_2$acyloxy benzoyloxy, $C_1$–$C_4$dialkylamino or heterocyclyl, or $C_3$–$C_4$alkenyl which is unsubstituted or substituted by 1–3 halogen atoms, $C_3$–$C_4$alkynyl, $C_3$–$C_6$cycloalkyl phenyl, benzyl or phenethyl, the phenyl rings of these compounds being unsubstituted or mono- to disubstituted by halogen, hydroxyl, $C_1$–$C_4$alkyl, halo-$C_1$–$C_2$alkyl, $C_1$–$C_2$alkoxy, halo-$C_1$–$C_2$alkoxy or nitro, or naphthyl or heterocyclyl, unsubstituted or mono- to disubstituted by identical or different substituents from the series consisting of halogen, $C_1$–$C_2$alkyl, halomethyl or nitro.

8. A compound of the formula I according to claim 7, in which:

$R_2$ is hydrogen, $C_1$–$C_5$alkyl, propenyl, phenyl or benzyl, the phenyl rings of these compounds being unsubstituted or mono- to disubstituted by halogen.

9. A compound of the formula I according to claim 2, in which:

Z is CO—$OR_2$.

10. A compound of the formula I according to claim 1, in which:

Z is CN or CO—$N(R_3)R_4$;

$R_3$ is hydrogen, $C_1$–$C_5$alkyl which is unsubstituted or substituted by 1–3 halogen atoms, $C_3$–$C_6$cycloalkyl, $C_1$–$C_2$alkoxy, phenoxy, hydroxyl, nitro, cyano, $C_1$–$C_2$alkanoyl, benzoyl, carboxyl, $C_1$–$C_4$alkoxycarbonyl, benzyloxycarbonyl, $C_1$–$C_2$acyloxy, benzoyloxy, $C_1$–$C_4$dialkylamino or heterocyclyl, or $C_3$–$C_4$alkenyl which is unsubstituted or substituted by 1–3 halogen atoms, or $C_3$–$C_4$alkynyl, $C_3$–$C_6$cycloalkyl, phenyl, benzyl or phenethyl, the phenyl rings of these compounds being unsubstituted or mono- to disubstituted by halogen, hydroxyl, $C_1$–$C_4$alkyl, halo-$C_1$–$C_2$alkyl $C_1$–$C_2$alkoxy halo-$C_1$–$C_2$alkoxy or nitro, or naphthyl or heterocyclyl, unsubstituted or mono- to disubstituted by identical or different substituents from the series consisting of halogen, $C_1$–$C_2$alkyl, halomethyl or nitro;

$R_4$ is hydrogen, $C_1$–$C_4$alkyl, $C_3$–$C_4$alkenyl $C_3$–$C_4$alkynyl, $C_3$–$C_6$cycloalkyl, phenyl or benzyl;

$R_3$ and $R_4$ together with the nitrogen atom to which they are bonded are pyrrolidine, piperidine, morpholine or dimethylmorpholine.

11. A compound of the formula I according to claim 10, in which:

Z is CO—N($R_3$)$R_4$;

$R_3$ is hydrogen, $C_1$–$C_5$alkyl which is unsubstituted or substituted by $C_1$–$C_4$alkoxycarbonyl or benzyloxycarbonyl, or $C_3$–$C_4$alkenyl, $C_3$–$C_4$alkynyl $C_3$–$C_6$cycloalkyl, phenyl or benzyl, the phenyl rings of these compounds being unsubstituted or mono- to disubstituted by halogen, hydroxyl, methyl, methoxy, halomethyl, halomethoxy or nitro;

$R_4$ is hydrogen or methyl; or $R_3$ and $R_4$ together with the nitrogen atom to which they are bonded are pyrrolidine, piperidine, morpholine or dimethylmorpholine.

12. A compound of the formula I according to claim 1, in which:

Z is CS—A;

A is $OR_2$, $SR_2$ or N($R_3$)$R_4$;

$R_2$ and $R_3$ are hydrogen, $C_1$–$C_5$alkyl which is unsubstituted or substituted by 1–3 halogen atoms, $C_3$–$C_6$cycloalkyl, $C_1$–$C_2$alkoxy, phenoxy, hydroxyl, nitro, cyano, $C_1$–$C_2$alkanoyl, benzoyl, carboxyl, $C_1$–$C_4$alkoxycarbonyl, benzyloxycarbonyl, $C_1$–$C_2$acyloxy, benzoyloxy, $C_1$–$C_4$dialkylamino or heterocyclyl, or $C_3$–$C_4$alkenyl which is unsubstituted or substituted by 1–3 halogen atoms, or $C_3$–$C_4$alkynyl, $C_3$–$C_6$cycloalkyl, phenyl, benzyl or phenethyl, the phenyl rings of these compounds being unsubstituted or mono- to disubstituted by halogen, hydroxyl, $C_1$–$C_4$alkyl, halo-$C_1$–$C_2$alkyl, $C_1$–$C_2$alkoxy, halo-$C_1$–$C_2$alkoxy or nitro, or naphthyl or heterocyclyl, unsubstituted or mono- to disubstituted by identical or different substituents from the series consisting of halogen, $C_1$–$C_2$alkyl, halomethyl or nitro;

$R_4$ is hydrogen, $C_1$–$C_4$alkyl, $C_3$–$C_4$alkenyl, $C_3$–$C_4$alkynyl, $C_3$–$C_6$cycloalkyl, phenyl or benzyl;

$R_3$ and $R_4$ together with the nitrogen atom to which they are bonded are pyrrolidine, piperidine, morpholine or dimethylmorpholine.

13. A compound of the formula I according to claim 2, in which:

Z is CN, CH=U or $CH_2$—V;

U is O, $NR_{10}$, N—$OR_6$ or N—N(=C)$_n$($R_7$)$R_8$;

V is halogen, hydroxyl, $C_1$–$C_4$alkoxy, $C_1$–$C_4$acyloxy, benzoyloxy or benzyloxy; and in which $R_6$, $R_7$, $R_8$ and $R_{10}$ are as defined in claim 2; and n is 0 or 1.

14. A compound of the formula I in which:

Z is CH(V)$_2$; and

V is $C_1$–$C_4$alkoxy or a 5- or 6-membered cyclic acetal.

15. A compound of the formula I according to claim 1, in which:

Z is CN, COOH, CHO, $CH_2OH$, $CH_2Cl$, $CCl_3$ $CHF_2$ or $CF_3$.

16. A compound according to claim 1 of the formula Ia

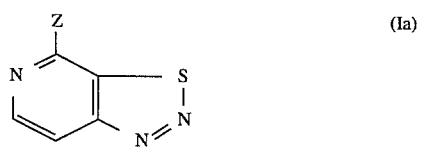

(Ia)

17. A compound according to claim 1 of the formula Ib

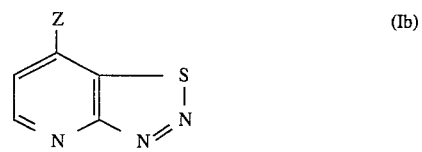

(Ib)

18. A process for the preparation of a compound of the formula Ia according to claim 16, which comprises reacting a compound of the formula II

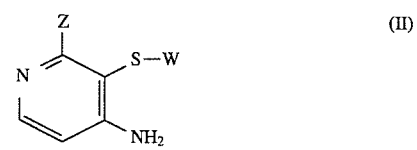

(II)

in which Z is as defined for formula I and

W is a substituted or unsubstituted $C_1$–$C_{12}$ hydrocarbon or a substituted or unsubstituted carbamoyl group, with an inorganic or organic nitrite in a suitable solvent.

19. A process for the preparation of a compound of the formula Ib according to claim 17, which comprises reacting a compound of the formula XXIII

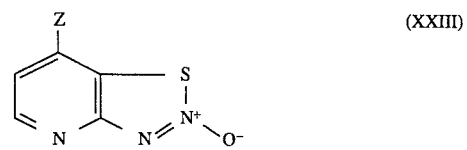

(XXIII)

in which Z is as defined for formula I, with a reducing agent.

20. A composition for protecting plants against attack by microorganisms, which comprises, as active ingredient, at least one compound according to claim 1 in free form or in agrochemically utilizable salt form together with a carrier material.

21. A method of protecting plants against attack by microorganisms, which comprises applying, as active ingredient, a compound of the formula I according to claim 1 to the plants, to parts of the plants and/or to the locus of the plants.

22. A method of immunizing plants against attack by microorganisms, which comprises applying, as active ingredient, a compound of the formula I according to claim 1 to the plants, to parts of the plants and/or to the locus of the plants.

23. A compound of the formula XXIII

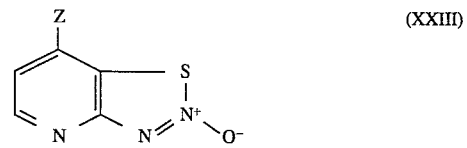

(XXIII)

in which Z is as defined for formula I.

* * * * *